US012690979B2

(12) United States Patent
Graham

(10) Patent No.: US 12,690,979 B2
(45) Date of Patent: Jul. 28, 2026

(54) SINUS TARSI IMPLANT

(71) Applicant: Michael Graham, Macomb, MI (US)

(72) Inventor: Michael Graham, Macomb, MI (US)

(73) Assignee: Graham Medical Technologies, L.L.C., Rochester, MI (US)

( * ) Notice: Subject to any disclaimer, the term of this patent is extended or adjusted under 35 U.S.C. 154(b) by 1596 days.

(21) Appl. No.: 17/109,121

(22) Filed: Dec. 1, 2020

(65) Prior Publication Data

US 2021/0128313 A1     May 6, 2021

Related U.S. Application Data

(63) Continuation-in-part of application No. 15/015,746, filed on Feb. 4, 2016, now abandoned.

(51) Int. Cl.
*A61F 2/42* (2006.01)
*A61F 2/30* (2006.01)

(52) U.S. Cl.
CPC .. *A61F 2/4202* (2013.01); *A61F 2002/30205* (2013.01); *A61F 2002/30224* (2013.01); *A61F 2002/30245* (2013.01); *A61F 2002/30754* (2013.01); *A61F 2002/30822* (2013.01); *A61F 2002/30828* (2013.01); *A61F 2002/4212* (2013.01)

(58) Field of Classification Search
CPC ............ A61F 2/4202; A61F 2002/4212; A61F 2002/30822; A61F 2002/30828; A61F 2/202
See application file for complete search history.

(56) References Cited

U.S. PATENT DOCUMENTS

| | | | |
|---|---|---|---|
| 4,450,591 A * | 5/1984 | Rappaport | A61B 17/562 |
| | | | 128/898 |
| 5,057,109 A | 10/1991 | Olerud | |
| 5,300,076 A | 4/1994 | Leriche | |
| 5,522,842 A | 6/1996 | Zang | |
| 5,522,843 A * | 6/1996 | Zang | A61B 17/8888 |
| | | | 606/232 |
| 6,053,920 A | 4/2000 | Carlsson et al. | |
| 6,136,032 A | 10/2000 | Perice et al. | |

(Continued)

OTHER PUBLICATIONS

Dockery et al., "The Maxwell-Brancheau Arthroereisis (MBA) implant in pediatric and adult flexible flatfoot conditions," Foot and Ankle Quarterly, Winter 1999, vol. 12, No. 4, pp. 107-120.

(Continued)

*Primary Examiner* — Christopher D. Prone
(74) *Attorney, Agent, or Firm* — Scott Houtteman; Houtteman Law, LLC

(57) ABSTRACT

A sinus tarsi implant for the purpose of stabilizing and restoring motion between the talus and calcaneus while allowing normal motion and alignment. In a preferred embodiment, the implant is composed of a titanium alloy that is a combination of a cylindrical portion and an axially connected conical portion. The cylindrical portion has a surface with multiple parallel grooves that are each parallel to the transverse axis of the cylinder. The grooves are uniquely shaped with a perpendicular medial side and an angled lateral side. The implant is cannulated to enable use of a guide wire that insures proper alignment during insertion.

13 Claims, 4 Drawing Sheets

(56)  References Cited

U.S. PATENT DOCUMENTS

| | | | |
|---|---|---|---|
| 6,168,631 B1 | 1/2001 | Maxwell et al. | |
| 6,443,954 B1 | 9/2002 | Bramlet et al. | |
| 6,607,535 B1 | 8/2003 | Chan | |
| 7,033,398 B2 | 4/2006 | Graham | |
| 8,628,581 B2 | 1/2014 | Zang et al. | |
| 2005/0177165 A1* | 8/2005 | Zang .................... | A61B 17/562 |
| | | | 606/301 |
| 2005/0187636 A1* | 8/2005 | Graham ................ | A61F 2/4225 |
| | | | 623/21.18 |
| 2005/0197711 A1* | 9/2005 | Cachia ................. | A61B 17/562 |
| | | | 623/908 |
| 2012/0041566 A1 | 2/2012 | Lenz et al. | |
| 2012/0191209 A1* | 7/2012 | Olson ................ | A61B 17/8625 |
| | | | 623/21.18 |

OTHER PUBLICATIONS

Stagni et al., "Role of passive structures in the mobility and stability of the human subtalar joint: a literature review," Foot & Ankle International, May 2003, vol. 24, No. 5, pp. 402-409.
MBA Subtalar Implant, Product Brochure, Kinetikos Medical Inc., Undated, 6 pages.

* cited by examiner

SINUS TARSI IMPLANT

BACKGROUND OF THE INVENTION

This invention relates to a medical apparatus for enhancing and for correcting skeletal mechanics. More specifically, this invention relates to the correction of certain bone alignment deformities that impair optimal biped mechanics.

Excessive pronation (hyperpronation) is caused by abnormal motion between two bones of the foot; the ankle bone (talus) and the heel bone (calcaneus). This abnormal motion will eventually lead to anatomical mal-alignment both proximally and distally. The abnormal motion is due to the partial dislocation of the talus on the calcaneus resulting in the obliteration or closure of a naturally occurring space (sinus) formed between the talus and calcaneus.

This sinus is referred to anatomically as the sinus tarsi. In anatomical terms, the sinus tarsi is located anterior to the posterior talocalcaneal joint and posterior to the middle and anterior talocalcaneal joint. As will be described in greater detail below, the talotarsal joint is formed by the articulations of the talus on both the calcaneus and navicular bones. The posterior talar facet of the calcaneus and the posterior calcaneal facet of the talus is the largest of the four talotarsal joint articulations. Generally speaking, when a human biped is walking or running, the individual's talus acts as a "torque converter" to transfer the weight of the body to the foot. This weight transfer is accomplished via the motion of the talotarsal joint. The normal mechanics of the talotarsal joint produces a triplanar motion-motion through all three anatomical planes. This motion consists of supination, and pronation. Pronation occurs when the talus moves medially (inward), anterior (forward) and plantarly (inferiorly). Supination occurs when the talus moves laterally (outward), posteriorly (backward) and dorsally (upward). Normally, there should be approximately a two-to-one ratio of supination to pronation.

Some individuals suffer as a result of abnormal motion of the subtalar joint. This partial dislocation leads to excessive pronation or, more specifically, hyperpronation. The pathomechanics of hyperpronation leads to significant deleterious effects to the bony architecture of the talus and calcaneus both proximally and distally. Hyperpronation is defined by excessive talar deviation medially (inward), anteriorly (forward), and plantarly (inferiorly).

Hyperpronation is detected and diagnosed through physical examination of the foot, both non-weight bearing and weight bearing examination, as well as radiographic evaluation of the foot. Non-weight bearing examination of hyperpronation is achieved by applying pressure to the fifth metatarsal head region of the foot to dorsiflex the foot (push the foot toward the front of the shin) and if the foot turns out-ward hyperpronation is present. In the weight-bearing examination, the person stands on his/her feet and the examiner observes both pronation and supination of the subtalar joint. Normally the foot should be in a "neutral" position, that is, neither pronated nor supinated. If the foot is in a pronated position while full weight is on the foot, the foot is considered hyperpronated.

Radiographic evaluation of partial talotarsal dislocation is seen by examining the weight-bearing anterior-posterior (top to bottom) view and the lateral (side) view. These two projections show the relationship of the talus to the other foot bones. If the talus is medially (inward) and/or anteriorly (forward) deviated and/or plantarflexed (inferiorly) partial talotarsal dislocation is present.

Previous implants have been designed for insertion into the sinus tarsi in an attempt to treat foot disorders. In this, one envisioned design included a mushroom-shaped implant with a stem protruding from the bottom. The implant was held in place by inserting the stem into a hole drilled into the dorsum of the calcaneus. Unfortunately, drilling can weaken the calcaneus and often resulted in direct or ultimate fracture. Moreover, the stem of the implant is subject to fracture which, of course, again leads to failure of the procedure. Also, the surgical procedures necessary for implantation is somewhat and subject to physician error.

In another previously known design, an implant is threaded on an outer surface and screwed into the sinus tarsi. This implant is usually composed of high molecular weight polyethylene. Unfortunately, this device can only be gas sterilized. This allowed the device to deform under the compressive pressure to which it is subjected under normal post-operative condition. Furthermore, it was difficult to accurately locate the device properly within the sinus tarsi.

In yet another design, a cylindrical implant made of a titanium alloy is threaded on an outer surface. However, this implant only corrects one portion of the deformity while both the lateral and medial portions of the sinus tarsi need correction. Furthermore, a titanium implant is much harder than surrounding bone matter. This can lead to bone wear and/or deformation. In addition, fluoroscopy is required in order to verify the position which exposes a patient to radiation. The procedure for insertion requires two separate incisions on the medial and lateral aspect of the foot and calls for a below-the-knee cast for two weeks postoperatively. The implant is made available in a series of sizes. These implants vary in size, one from the next, by specific increments. Gaps in this series can lead to under and over correction. Finally, prior art implants are threaded on their outer surface. Without any special structure to these threads, the implant can loosen and pop out of place.

The problems suggested in the preceding are not intended to be exhaustive but rather are among many which may tend to reduce the effectiveness of sinus tarsi implants known in the past. Other noteworthy problems may also exist; however, those presented above should be sufficient to demonstrate that previously known sinus tarsi implants will admit to worthwhile improvement.

OBJECTS OF THE INVENTION

The following "objects" apply to preferred embodiments of the invention and do not limit the invention in any way. It is a general object to obviate limitations in correcting abnormal foot mechanics of the type previously described.

An object is to insure proper foot motion by stabilizing the motion between the talus and calcaneus. A related object is to insure that both the medial and lateral aspects of these bones are stabilized.

Another object is to stabilize motion between the talus and calcaneus and/or navicular while allowing normal foot motion.

A further object is to correct mal-alignment, both proximally and distally, of the talus and calcaneus.

Another object is to provide an implant that will not, over time, wear or deform the talus and calcaneus.

Still another object is to provide an implant that will not wear or deform over time and thus fail.

Another object is to provide an implant that will remain in place after extended wear without a separate anchoring procedure.

Another object is a method of correctly positioning an implant in the space between the talus and calcaneus bones without having to verify the correct position with a fluoroscope and thus expose the user to radiation.

A further object is to provide less invasive surgery for inserting an implant.

A related object is to provide a sinus tarsi implant without requiring a post-operative below-the-knee cast.

BRIEF SUMMARY OF THE INVENTION

An embodiment of the present invention that is intended to accomplish at least some of the foregoing objects comprises stabilizing or restoring normal motion of the subtalar joint with an internally placed endoprosthesis device. In medical terms, this embodiment comprises a subtalar endorthosis implantation system. The implant is termed a subtalar or, more specifically, a sinus tarsi stent which maintains the sinus tarsi in an anatomically correct alignment, allowing the normal physiological motion to occur while minimizing a tendency for abnormal pre-operative motion.

The sinus tarsi implant of the subject invention is generally a conically shaped with an integral cylindrically shaped extension. The conical portion is considered the superficial or lateral portion of the implant and may be operably positioned within the lateral or sinus region of the sinus tarsi. The small diameter cylindrical portion of the implant is considered the medial side of the implant and will be operably positioned within a deeper side of the sinus tarsi, the canalis tarsi.

The surface of the implant optionally contains a series of parallel ridges and channels on the outer surface of the implant. These surface regions will, in a preferred embodiment, interact with the surrounding tissue and increase the mechanical retention between the surface of implant and the surrounding tissue and thus helps maintain the implant in a proper anatomical position.

The sinus tarsi implant of the subject invention is preferably constructed of a titanium alloy, the standard material used for implants. A medical grade polymer, however, will also function. The polymer composition will allow for less trauma to the external bone surface as compared to the titanium alloy based implant. The implant optionally has a hole bored through its longitudinal axis (a cannula) that allows for accurate placement into the sinus tarsi via a guide wire or guide peg.

BRIEF DESCRIPTION OF THE DRAWINGS

Other objects and advantages of the present invention will become apparent from the following detailed description of preferred embodiments taken in conjunction with the accompanying drawings wherein.

DETAILED DESCRIPTION OF THE INVENTION

Figure 1:
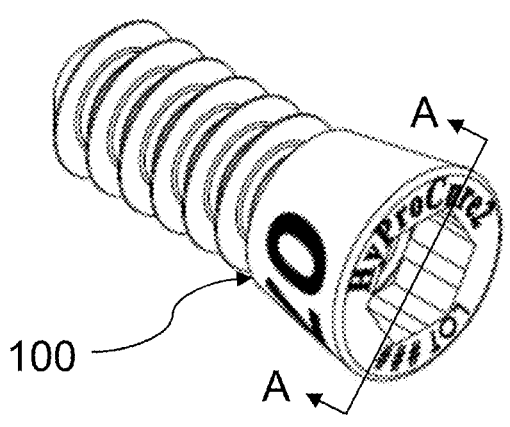
FIG. 1 is a perspective view of the sinus tarsi implant.

Referring now to the drawings wherein like numerals indicate the parts, FIG. 1 is a perspective view of the implant 100.

Figure 2:
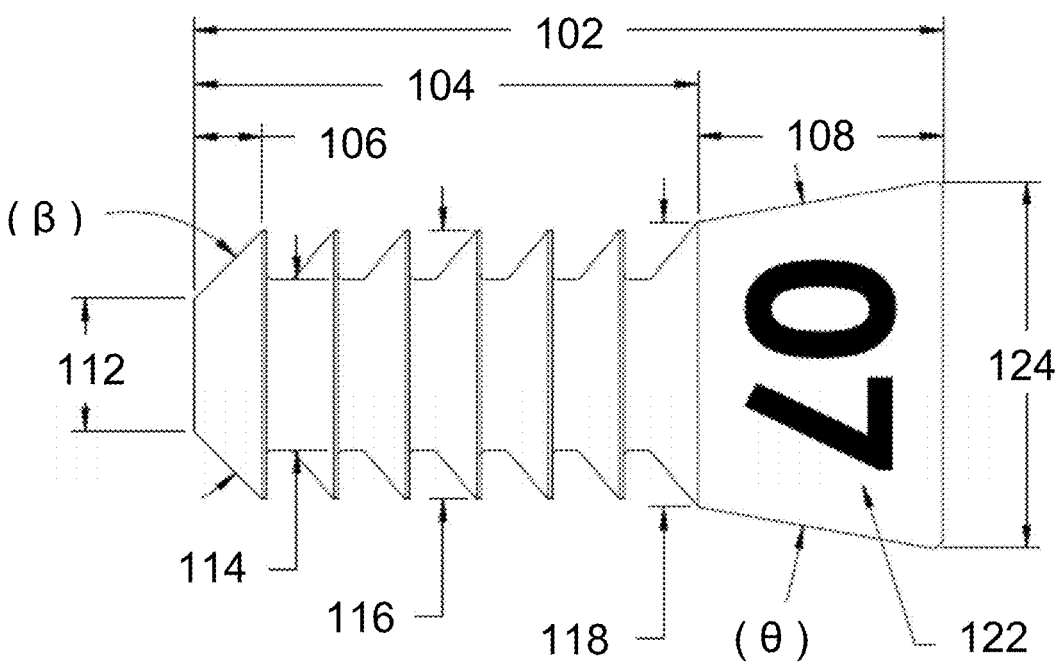
FIG. 2 is a side view of the implant.

FIG. 2 depicts a side view of the implant. A preferred overall length of the implant is about 17 to 19 mm, more preferably about 18.34 mm. The implant has a cylindrical body portion 104 preferably 11 to 14 mm long, more preferably about 12.34 mm long. The implant also has a conical foot portion 122, 212. The foot has a relatively small top end 118 which is integrally connected to the cylindrical body. The foot flairs out to form a relatively larger circular base 124. Viewed from the side (FIG. 2) these two sides of the foot flair out together to form an angle, 0. This angle, 0, is preferably about 15° to 25°, or preferably each angle from 15° to 25° in 0.1° degree increments, or more preferably about 19.8°.

In order to properly block abnormal motion while allow normal motion, the implant 104 must have a carefully chosen outer diameter 116, 118, 124. The absolute size of the implant will vary depending on the size of the ankle into which the implant is inserted. The diameter at the top of the foot is in the preferable range from 5 to 14 mm, more preferably from 6 mm to 13 mm, still more preferably from 7 to 12 mm. The diameter of the base of the foot will be proportionally larger. For ease of identification, these diameters can be affixed to the implant, for example on the outer surface of the foot. The standard error of these dimensions will be about 0.05 mm.

Turning now to the cylindrical body, the surface will have a plurality of parallel grooves as shown in FIG. 2, 114. In a preferred number of grooves is 3 to 9, more preferred 4 to 8, still more preferred, 5 to 7, yet still more preferred 6 grooves. The bottom of the groove will have a preferable diameter 114 that maximizes the ability of the implant to promote stability, for example, by allowing soft tissue ingrowth but without being so deep as to weaken the structural integrity of the body. A preferred diameter at the groove bottom is about 4 mm. In another preferred embodiment, the diameter at the groove bottom varies so that the depth of the grooves is kept constant as the size of the implant varies. A preferred grove depth is about 2 nun. In another preferred embodiment, the diameter of the implant is kept constant and the depth of the grooves varies with the size of the implant.

Inter-groove portions of the body 116 will have about the same diameter as the junction between the body and the foot 118. At the medial end of the body a cannula (or tunnel) 112 can optionally be drilled into the implant. This allows the use of a guide wire which can run through the cannula and promote proper orientation of the implant during insertion. At the medial end of the body, on either side of the cannula, the end surface of the implant will form an angle, f, as shown in FIG. 2 which is preferably about 90°.

Figure 3:
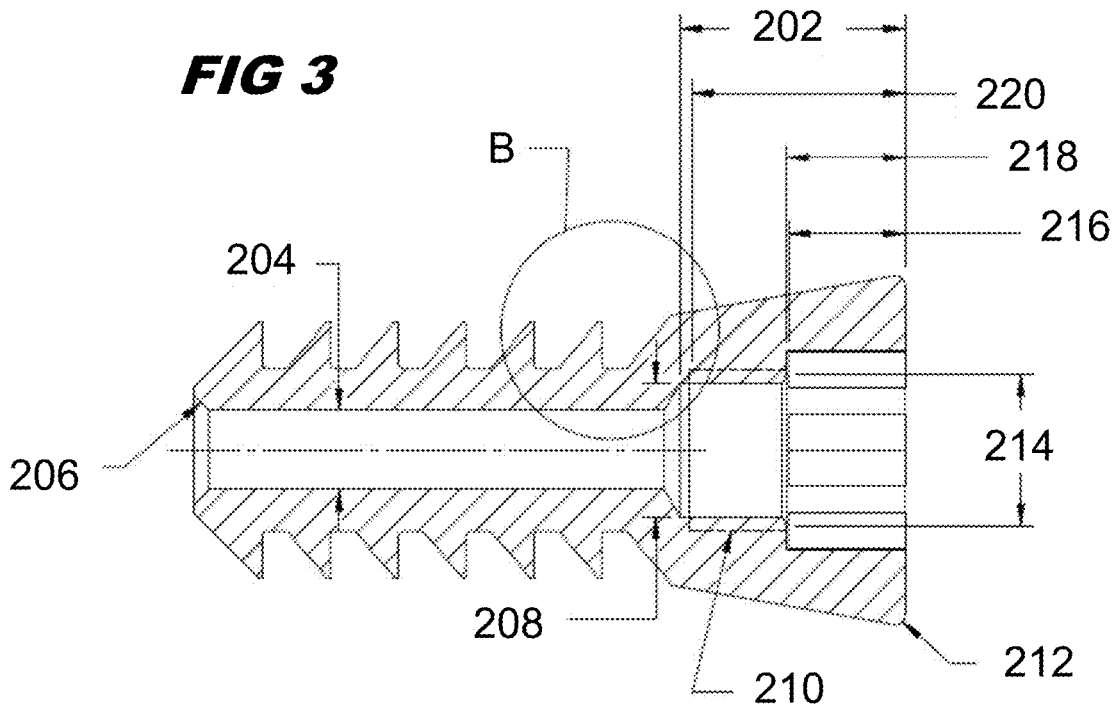
FIG. 3 is a cross-sectional view of the implant taken along section line A-A in FIG. 1.

FIG. 3 illustrates a cross section taken along line A-A as shown in FIG. 1 highlighting some internal structures of the implant. The cannula inner diameter 204 is shown. Also, at the medial end of the implant, the inner surface (the cannula) flares out to meet the sloping outer surface 106. Accordingly the lateral end of the implant is preferably not flat but in the form of a pointed circular ridge.

The implant is usually slid into place without turning. The lateral end of the implant can have a specialized structure to aid in insertion. Located at the base of the foot portion 212, this end, in a preferred embodiment, is provided with a recess and internal surface structure 202, 220, 218, 216, 210, 208 having a selected geometric shape. These structures are configured to accept the end of an insertion tool having a complementary geometric shape. Preferably, the tool would be inserted into the recess and used to advance the implant into position. Any geometric shape can be used, preferably a shape in which maximum torque can be applied without slippage. Examples, of suitable shapes include straight slots (flat heads), cruciate (PHILLIPS heads), hexagonal, POSI-DRIVE, TORX, Allen-type and others.

Figure 4:
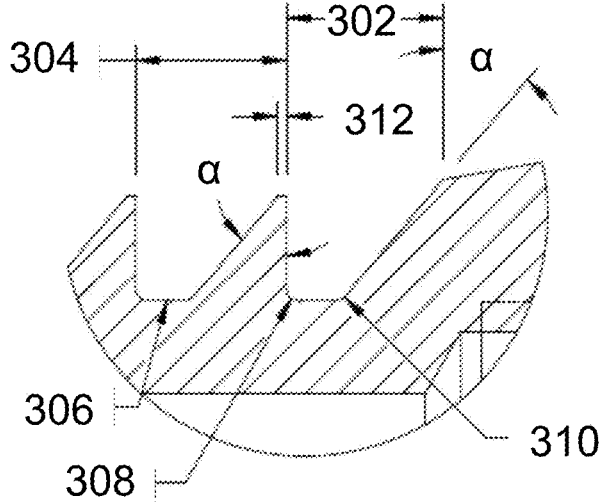
FIG. 4 is an enlarged view of detail "B" from FIG. 3.

FIG. 4 is an enlarged view of detail B of FIG. 3, highlighting one of the groves in the outer surface of the implant's cylindrical body. A single groove has a length 304 which is the sum of the width of the gap at the surface 302 plus the width of the surface strip between the grooves 312. The medial side of a groove, which is perpendicular to the central axis of the implant, makes an angle, a, with the lateral side of the groove as shown. The lateral side adjacent to the implant foot preferably forms the angle, a with a line perpendicular to the implant central axis. The angle a is, preferably, about 45°. The bottom of the groove is indicated 306. The medial corner 308 and the lateral corner 310 are preferably rounded rather than cut at sharp angles as is shown.

Figure 5:
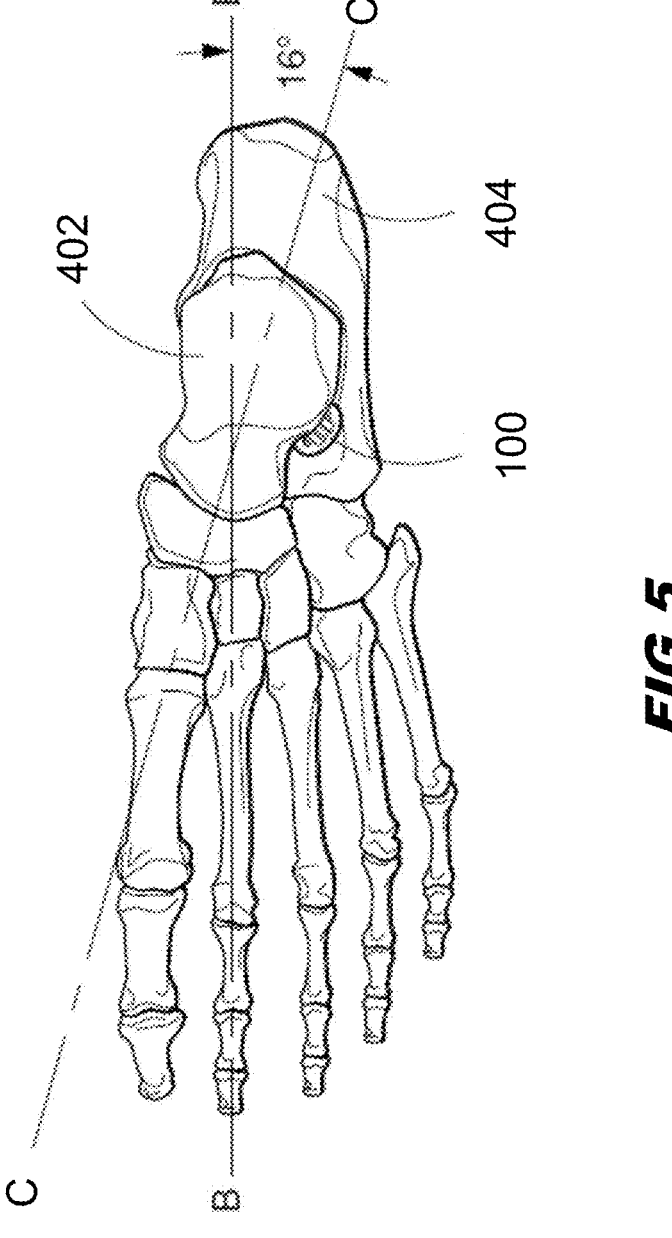
FIG. 5 is a dorsal view of the bone structure of a human foot with a sinus tarsi implant in situ displaying the axis of rotation of the subtalar joint relative to the midline.
Figure 6:
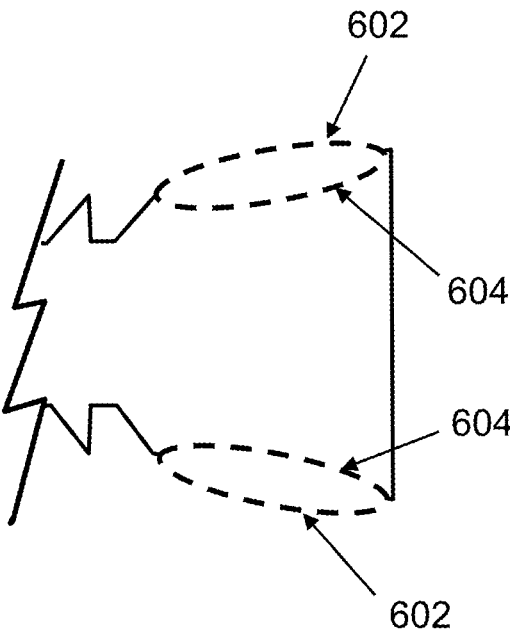
FIG. 6 is an illustration of generic convex 602, hemispherical 602 and concave 604 side surfaces of the implant's conical foot portion.

FIG. 5 illustrates the implant in situ. As described previously, the implant 100 operates by arthroeresis (blocking of motion) of the patient's subtalar joint. The subtalar joint is the articulation between the talus 402 superiorly and the calcaneus 404 inferiorly. FIG. 5 also illustrates an axis C-C of subtalar joint motion which is approximately 16 degrees measured from a midline axis B-B of a human foot.

Turning now to the compositions from which the implant is made, the subject invention is intended to provide a long term implant with expected useful life ranging from a period of years to a period of decades. Moreover, the subject invention is intended to be operably a permanent implant; one that will rarely or preferably never require replacement over the lifetime of the user. In this, the selected material of an implant 100 must be soft enough so as to prevent excessive wear and deformation of the surrounding bones causing undesirable side effects but, concomitantly, durable enough so that the implant itself will not excessively wear and deform and eventually fail or require premature replacement.

In a preferred embodiment, an implant is made entirely from a single substance. In another preferred embodiment, the implant composition preferably comprises a medical grade polymer suitable for the insertion in the body in that it is substantially inert with respect to chemical reactions present in the body and is unlikely to result in adverse reactions, infections, adverse immunologic reactions such as allergic reactions or rejection. In another preferred embodiment the implant is medical grade titanium alloy. Still another preferred embodiment is a medical grade polymer suitable for long term or permanent implantation as defined above. It is presently envisioned that the implant composition will comprise suitable polymers such as medical grade polyetheretherketone (PEEK), polyetherketoneketone (PEKK), polymethyl-methacrylate (PMMA), polytetrafluoroethylene (PTFE), crystalline plastics, polyoxymethylene and DELRIN.

The implant composition need not be a single substance. Indeed it is envisioned that compositions comprising blends of two or more substances will be suitable. Suitable blends include combinations of polymer fibers dispersed in resins such as DELRIN AF, a blend of PTFE fibers uniformly dispersed in DELRIN acetal resin.

Polymer research has resulted in the development of scores of high grade polymers. These polymers have physical properties that cover the entire range of properties (such as durability and hardness) from metallic and plastic. Accordingly, it is envisioned that many other compositions will be suitable for use with this implant so long as these compositions have the desired properties.

It is also contemplated that multiple substances can be combined to form a hybrid implant combining the advantageous properties of each substance. For example, more durable substances can be combined with more flexible substances. High coefficient of friction substances can be combined with low coefficient of friction substances. These substances can be placed in specific portions of the implant where the corresponding property is most critical. Alternatively, the substances can be blended together in a uniform ratio throughout the entire implant.

Also, while post operative imaging (fluoroscopic, magnetic resonance imaging, etc) is not needed for proper placement of the implant, imaging may be desired for special purposes. In such cases, an opaque structure can be imbedded into the implant or an opaque substance added to the polymer for the purposes of imaging.

It is important to note that in cases where the bone surrounding the implant is protected from wear then harder, more durable materials can be used including metal alloys. For example, biotechnological techniques to stimulate growth of bone cells (osteogenesis) and thus replace worn regions of bone can permit the use of harder materials. Of course, if the implant is only required for a short time then the material from which the implant is made is less critical.

In the context of this invention, terms such as "generally shaped," "generally configured in the shape," "generally cylindrically configured" etc. are meant to indicate that the implant may, but need not be shaped so as to conform to strict definitions from solid geometry for solids such as "cylinders" and "cones."

Indeed, in order to provide an implant with the proper size and shape for every patient, a range of sizes and shapes are contemplated. At one extreme, a "standard set" is utilized where a set of "consensus" sizes and shapes implants are pre-manufactured and provided to health care providers and their patients. This particular embodiment has the advantage of being the most uniform and therefore the least expensive for the patient.

At the other extreme, a "custom design" is envisioned where the exact size and shape is determined only after precise, detailed measurements of the inner dimensions of a patient's sinus tarsi. As a result, the generally cylindrical portions of the implant may be tapered or shaped if necessary; however, the general cylindrical configuration will remain.

In one embodiment, a range of sizes of the implant will be provided. As described herein, the size of the implant can be varied in different ways: (1) all dimensions of the implant vary proportionally; (2) the overall implant size is varied but the depth of the grooves is be kept constant; and (3) as the overall implant size increase the groove depth increases at a greater rate.

The size and shape of the foot portion of the implant is critical only at the point where the implant contacts the surrounding ankle bones; the calcaneus below the implant and the talus above the implant. Accordingly, the sides of the foot portion, which are generally conically shaped, may be concave or convex in appropriate regions. (Note, however, that the general funnel configuration will remain.) The sides can even be hemispherical. The radius of the sphere being the radius of the circular base portion. Thus, the overall size of the foot portion can be altered so that the hemispherical foot implant has the same dimensions as the conical foot at the points where the foot contacts the surrounding bone.

In a preferred embodiment, the conical sides of the foot portion 122 of the implant flare out, from the top to the base 118 to the foot 124. The flaring sides together form an angle, 0. In a preferred embodiment 0 is in the range of 15° to 25°. In another preferred embodiment 0 is in the range of 19.3° to 20.3°. In still another preferred embodiment, 0 is selected from the group consisting of each of the angles from 15° to 25° in increments of 0.1°. (A set of about 100 specific angles.) In another preferred embodiment the angle, 0, is 19.8°.

The lateral end of the implant, which is the base of the foot portion, does not contact the ankle bones. Because of this, additional material can be added to this end, in virtually any shape, without significantly affecting function. Adding material here is not recommended because it would merely add expense without providing any functional improvement.

In effect, with the custom design method there are as many different shapes and sizes as there are patients. The custom design embodiment has advantages such as the patient receiving a precise amount of arthroeresic correction (degree of blocking of abnormal motion) which could be critical in special cases, for example elite athletes, dancers and others whose occupations place unusual stresses on this region.

Thus, the actual number of different sizes and shapes of implants to be manufactured will ultimately depend upon economic considerations. If cost is the predominant factor than a relatively small number of different sized and shaped implants will be manufactured. In a preferred embodiment, applicant will provide a set of implants that vary in size from 5 mm to 14 mm, as measured from the top end 118 of the foot. On the other hand, as precision fit becomes a more dominant factor, then the number of different sizes and shapes available will increase accordingly, perhaps to a very large number.

In addition to the shape of the implant overall, the shape of the transition between the cylinder and frustum can also vary. This transition need not be abrupt as depicted, for example in FIG. 2, in the line between the sides of the foot portion 108 and the lateral end of the cylindrical portion 118. Rather, the transition could be smooth and gradual leaving no sharp "edge."

Surgical Procedures and Instrumentation

Instrumentation of this system includes a set of cannulated probing devices, a set of implants, a cannulated insertion tool and a guide wire or guide pin. In a preferred embodiment the probing devices have a diameter ranging from 5 mm to 12 mm to correspond to the size implant required for correction. Each probing device is increased in diameter by 1 mm.

The sinus tarsi implants are preferably provided in a set that range in size. Measuring from the outer diameter of narrow part of the implant (the second member) the set will, preferable, have a gauge from 0.5 cm to 1.2 cm. Implant size should, preferably, increase 1 mm in diameter from 0.5 cm to 1.2 cm.

A cannulated insertion tool is also included to advance the implant into the sinus tarsi. In a preferred embodiment, the insertion tool functions much like a screw driver as described below.

A preferred operative procedure consists of making a 1 cm to 2 cm linear incision over the sinus tarsi parallel to the relaxed skin tension lines. The incision is deepened via blunt dissection to the sinus tarsi.

The proper angle along which the implant is inserted into the patients sinus tarsi is then determined with one of the probing devices. The 0.5 cm cannulated probing device is inserted into the sinus tarsi from lateral distal dorsal to medial proximal plantar until it is palpated exiting the medial aspect of the sinus tarsi. The angle of the probing device is the proper angle along which the implant is inserted.

A guide (preferably a guide wire or a guide pin) is then inserted into the cannula of the probing device and is left in place until the end of the procedure. Starting with the smallest diameter probe (0.5 cm) subsequent larger sized probes are inserted over the guide until the appropriate size implant is determined.

As noted above, the implant 100 is cannulated (fashioned with a central longitudinal hole or cannula) 204 so that the implant can be placed on the guide followed by the cannulated insertion tool. Through the action of the insertion tool, the implant is then advanced into the sinus tarsi until proper placement is achieved. Correct placement of the implant occurs when the foot portion 108 abuts the lateral most aspect of the canalis tarsi. (The beginning or outermost aspect of the canalis tarsi.) Alternatively, placement can be achieved when the cylindrical body portion 104 abuts the lateral aspect of the talus, the sulcus tali.

After the implant is fully inserted the incision is closed. The method of closure of the incision is surgeon's choice.

SUMMARY OF MAJOR ADVANTAGES OF THE INVENTION

After reading and understanding the foregoing description of preferred embodiments of the invention, in conjunction with the illustrative drawings, it will be appreciated that several distinct advantages of the subject implant system are obtained.

Without attempting to set forth all of the desirable features and advantages of the implant and associated methods, at least some of the major advantages of the invention are the stabilization of both the medial and lateral aspects of the talus and calcaneus by the corresponding segments of the implant in contact with these regions which results in blocking hyperpronation of the foot while allowing normal motion.

Another advantage is the long useful lifetime of the implant. When the implant is made of the correct material, it will neither wear the surrounding bones nor will the implant wear.

A related advantage that also increases the lifetime of the implant is the permanent anchoring of the implant by way of the peripheral channels and threading. Failure due to slippage out of position will be rare or absent. Also, the surrounding bones remain strong as compared to procedures in which anchoring is achieved by drilling a hole into the calcaneus or the use of other invasive anchoring methods. As a result, complications stemming from weak surrounding bones are unlikely.

A still further advantage of the implant system is the ability to accurately position the implant without irradiation. The implant is correctly positioned when the implant abuts the lateral most aspect of the canalis tarsi or the sulcus tali or both. Thus, there is no need for a fluoroscope (and irradiation of the user's foot) to verify the positioning.

Another advantage of the subject sinus tarsi implant is primary correction of talotarsal dislocation, hyperpronation, talipes valgus, pes planus, and other related rearfoot and forefoot deformities. The implant will also be used for secondary correction of growing pains, shin splints, posterior tibial tendon dysfunction, plantar fasciitis, hallux abductovalgus, metatarsus primus varus and elevatus, metatarsus adducts, contracted toes, abnormal gait, intermetarsal neuromas, as well as sciatica, patellofemoral pain, genu varum anterior pelvic tilt, lumbar lordosis, etc.

Yet, another advantage is that the implant is inserted via a minimally invasive procedure and no casting is needed following the procedure so that there is a quick recovery.

In describing the invention, reference has been made to preferred embodiments. Those skilled in the art and familiar with the disclosure of the subject invention, however, may recognize additions, deletions, substitutions, modifications and/or other changes which will fall within the purview of the invention as defined in the following claims.

What is claimed is:

1. A sinus tarsi implant for use in correcting anatomical alignment of a patient's ankle bone structure comprising:

a cylindrical body portion consisting of a cylindrical side surface, a circular medial end and a circular lateral end, said medial and lateral ends being perpendicular to an implant central axis, said cylindrical side surface comprising a plurality of continuous circumferential grooves each perpendicular to the implant central axis, and a conical foot portion comprising a generally conical side surface, a circular top and circular base, said top being integrally connected, along the implant central axis, with the lateral end of the body portion, said conical side surfaces flare out to form an angle, θ, wherein θ is in the range 15° to 25° wherein said implant is capable of insertion into a patient's ankle and corrects anatomical alignment of the patient's ankle bone structure.

2. The sinus tarsi implant of claim 1 further comprising:
said base is fashioned with a recess configured to accept a tool so that when the tool is inserted into the recess the tool is operable to advance the implant into a proper position.

3. The sinus tarsi implant of claim 1 further comprising:
a longitudinal bore traversing the entire length of the implant along the implant central axis and fashioned to allow placement of the implant on a guide to facilitate proper surgical implantation.

4. The sinus tarsi implant of claim 1 further comprising:
an outer diameter, measured at the top of the conical foot, in a range from 5.0 mm to 12 mm.

5. The sinus tarsi implant of claim 1 further comprising:
each of said plurality of grooves consisting of a groove lateral side, a groove bottom and a groove medial side, said groove medial side being generally perpendicular to the implant central axis and said groove lateral side sloping outward from the groove lateral side at an angle, a, where a is in the range 35° to 45°.

6. The sinus tarsi implant of claim 5 further comprising:
said angle α is about 40°.

7. The sinus tarsi implant of claim 6 further comprising:
said cylindrical body portion has a diameter, measured from the top of a first groove to the top of a second groove positioned opposite the first groove, in the range of 5.0 mm to 10.0 mm.

8. The sinus tarsi implant of claim 6 further comprising:
said groove bottom is about 0.8 mm wide.

9. The sinus tarsi implant of claim 1 further comprising:
said plurality of grooves are in the range of four to eight grooves.

10. The sinus tarsi implant of claim 1 further comprising:
said plurality of grooves is six grooves.

11. The sinus tarsi implant of claim 1 further comprising:
said generally conical side surface is curved to form a convex surface.

12. The sinus tarsi implant of claim 11 further comprising:
said convex surface is hemispherical.

13. The sinus tarsi implant of claim 1 further comprising:
said generally conical side surface is hollowed inward to form a concave surface.

* * * * *